United States Patent
Yook et al.

(10) Patent No.: US 11,033,518 B2
(45) Date of Patent: Jun. 15, 2021

(54) PHARMACEUTICAL COMPOSITION CONTAINING NICLOSAMIDE FOR TREATING AXIN-GSK3 INTERACTION-RELATED DISEASES

(71) Applicant: BAOBAB PHARM CO., LTD., Seoul (KR)

(72) Inventors: Jong In Yook, Seoul (KR); Hyun Sil Kim, Seoul (KR); Nam Hee Kim, Seoul (KR); Kyoung Tai No, Seoul (KR); Ji Won Choi, Seoul (KR); Tae Il Kim, Seoul (KR); Sung Yong Ahn, Seoul (KR)

(73) Assignee: BAOBAB PHARM CO., LTD., Seoul (KR)

( * ) Notice: Subject to any disclaimer, the term of this patent is extended or adjusted under 35 U.S.C. 154(b) by 0 days.

(21) Appl. No.: 16/475,875

(22) PCT Filed: Jan. 9, 2018

(86) PCT No.: PCT/KR2018/000394
§ 371 (c)(1),
(2) Date: Jul. 3, 2019

(87) PCT Pub. No.: WO2018/128515
PCT Pub. Date: Jul. 12, 2018

(65) Prior Publication Data
US 2019/0343783 A1    Nov. 14, 2019

(30) Foreign Application Priority Data

Jan. 9, 2017    (KR) ................. 10-2017-0002868

(51) Int. Cl.
*A61K 31/167*    (2006.01)
*A61P 31/04*    (2006.01)
*A61P 35/00*    (2006.01)

(52) U.S. Cl.
CPC ............ *A61K 31/167* (2013.01); *A61P 31/04* (2018.01); *A61P 35/00* (2018.01)

(58) Field of Classification Search
CPC ......... A61K 31/167; A61P 31/04; A61P 35/00
See application file for complete search history.

(56) References Cited

U.S. PATENT DOCUMENTS

| | | | |
|---|---|---|---|
| 2011/0183889 A1 | 7/2011 | Fogelman et al. | |
| 2016/0136123 A1 | 5/2016 | Deretic et al. | |

FOREIGN PATENT DOCUMENTS

| | | |
|---|---|---|
| KR | 2012-0131401 A | 12/2012 |
| WO | WO-2004-006906 A2 | 1/2004 |
| WO | WO-2012-143377 A1 | 10/2012 |

OTHER PUBLICATIONS

Chowdhury et al., Niclosamide block glucagon phosphorylation of Ser552 on beta-catenin in primary rat hepatocytes via PKA signalling. Biochem. J., vol. 473, pp. 1247-1255 (Year: 2016).*
Ahn, Sung Yong. "Regulation of Cancer EMT by Axin-GSK3 Interaction Inhibitor." The Doctoral Dissertation Submitted to the Department of Applied Life Science and the Graduate School ofYonsei University, 2016, pp. 1-IX, 1-63.
Batlle, E., et al., Nature Cell Biol, 2000, 2, 84-89.
Cano, A., et .al., Nature Cell Biol, 2000, 2, 76-83.
Dajani, R., et al., EMBO J., 2003, 22, 494-501.
Du, et al., Cancer Res. 2010, 70, 10080-10089.
Gupta, PB, et al. Cell 2009, 138, 645-659.
Half, E., et al., Orphanet J Rare Dis., 2009, 4, 22.
International Search Report (ISR), dated Apr. 13, 2018, issued for International Patent Application No. PCT/KR2018/000394, with English translation.
Kim, NH, et al., Sci Signal., 2011, 4(197), ra71.
Kim, NH, et al., J Cell Biol, 2011, 195, 417-433.
Lee, et al., Nature Communications 2014, 5, 4423.
Leonardo, et al., Helicobacter 2014, 19, 1-5.
Li, Y., et al., Cancer Lett., 2014, 349, 8-14.
Liang, L., et al., Inflammation Research, 2015, 64, 225-233.
Lyons, et al., Cancer Res, 2008, 68, 4525-4530.
Maheshwari, M., et al., Biochemistry, 2010, 49, 10371-10380. Doi: 10.1021/bi101249p.
Minde, DP., et al., Mol Cancer. 2011. 10. 101.
Morin, F., et al., J Immunol, 2016; 197:3018-3028; Prepublished online Sep. 9, 2016; doi: 10.4049/jimmunol.1502482; http://www.jimmunol.org/content/197/8/3018.
Morin, F., et al., J Invest Dermatol. 2016, 136(11), 2158-2167.
Osada, T., et al., Cancer Res. 2011, 71(12), 4172-4182.
Sack, U, et al., J Natl Cancer Inst., 2011, 103, 1018-1036.
Tao, H., et al., Nat Med. 2014, 20(11), 1263-1269.
Wang, YC., et al., PLoS One., 2013, 8, e74538.
Yook, JI, et al., JBC 2005, 280, 11740-11748.
Yook, JI, et al., Nature Cell Biol, 2006, 8, 1398-1406.

* cited by examiner

*Primary Examiner* — Barbara P Badio
(74) *Attorney, Agent, or Firm* — Harness, Dickey & Pierce, P.L.C.

(57) ABSTRACT

The present invention relates to a pharmaceutical composition containing, as an active ingredient, niclosamide or pharmaceutically acceptable salts thereof, for treating or preventing disease related to Axin-GSK3 interaction, such as familial adenomatosis polyposis (FAP). According to the present invention, familial adenomatosis polyposis (FAP) which causes pain due to lack of specific treatment methods, can be effectively treated using niclosamide, which is a safe drug approved by the FDA.

2 Claims, 13 Drawing Sheets

A

B

PHARMACEUTICAL COMPOSITION CONTAINING NICLOSAMIDE FOR TREATING AXIN-GSK3 INTERACTION-RELATED DISEASES

CROSS-REFERENCE TO RELATED APPLICATIONS

This application is a national phase application of PCT Application No. PCT/KR2018/000394, filed on Jan. 9, 2018, which claims the benefit and priority to Korean Patent Application No. 10-2017-0002868, filed on Jan. 9, 2017. The entire disclosures of the applications identified in this paragraph are incorporated herein by references.

FIELD

The present invention relates to a pharmaceutical composition for treating Axin-GSK3 interaction-related diseases comprising niclosamide, and more specifically, relates to a use for treatment or prevention of Axin-GSK3 interaction-related diseases such as familial adenomatosis polyposis (FAP), multiple colonic polyps, inflammation by *Helicobacter pylori*, or gastric cancer using niclosamide or its pharmaceutically acceptable salt as an active ingredient.

BACKGROUND

Epithelial-mesenchymal transition (EMT) is a biological mechanism which induces invasiveness and stemness resistant to treatment in human cancer, and methods for treating cancer by recovering EMT with a low molecular inhibitor have been researched. Salinomycin has been known to recover EMT of cancer cells effectively, and it has been reported to inhibit cancer differentiation with potency up to 100 times in proportion to the representative anticancer agent, paclitaxel and inhibit metastasis of breast cancer in vivo experiment (Gupta P B, et al., Cell., 138:645-6592, 2009). Although salinomycin cannot be used for human, this result suggests a new strategy for cancer treatment which controls EMT in human cancer.

A transcriptional factor, Snail causes EMT by inhibiting a gene of epithelial tissue in human cancer (Cano A. et al., Nature Cell Biol, 2, 76-83, 2000; Bathe E et al., Nature Cell Biol, 2, 84-89, 2000). The major carcinogenesis pathway of Wnt signal, p53 tumor suppression gene, and CagA protein that is a bacterial carcinogen of *H. pylori* controls Snail activity through post-translation and post-transcription mechanisms (Yook J I et al., J Biol Chem, 280, 11740-11748, 2005; Kim N H et al., J Cell Biol 195, 417-433, 2011; Lee et al., Nature Communications, 5:4423, 2014). Also, β-catenin and Snail transcription mechanisms are phosphorylated and degraded by GSK3. Furthermore, Wnt signal or CagA blocks phosphorylation and thereby increases TCF transcriptional activity and progresses Snail-mediated EMT. The GSK3 scaffolding protein, Axin2 controls nucleo-cytoplasm shuttling of GSK3 to function to control this process (Yook J I et al., Nature Cell Biol, 8, 1398-1406, 2006). As a result, nuclear Snail increased in cancer cells happens. Interestingly, the GSK3 shuttling function by Axin is required for phosphorylation of membrane LRP6 Wnt receptor and next activation of intracellular Wnt signal activity. Like this, the Axin-GSK3 complex plays an important role to control Wnt signal and Snail-mediated EMT program. Conversely, inhibition of Axin-GSK3 complex may be a new MoA (mode of action) in the development of a low molecular inhibitor targeting Wnt signal and Snail-mediated EMT program of human cancer.

*Helicobacter* (*Helicobacter pylori*) is a representative carcinogenic bacterium living in the gastrointestinal tract of humans. The World Health Organization (WHO) defines *Helicobacter* as a definite carcinogen bacterial infection. *Helicobacter* exhibits the prevalence of 30-40% in the West and 70% or more in underdeveloped countries, and its infection occurs in 50% or more of the population in Korea (Leomardo et al., *Helicobacter*, 19, supple1:1-5, 2014). *Helicobacter* causes inflammation of gastrointestinal mucosa by infecting stomach and intestine of human, and further, it is an important cause of gastric cancer. *Helicobacter* infects stomach and intestine and injects cytotoxin-associated gene A (CagA) protein in gastric mucosa cells and such CagA plays an important role in inflammation of gastrointestinal mucosa cells and cancer occurrence. Recently, it has been discovered that CagA conducts a similar function with Axin. Specifically, When *Helicobacter* injects CagA to epithelial cells, CagA binds to GSK-3 similarly to Axin and through this, the GSK-3 kinase function is inhibited and further Snail expression increases (Lee et al., Nature Communications, 5:4423, 2014). In initial researches, it has been known that Snail expression increases during the cancer metastasis process, but according to the recent result, it has been known that Snail directly induces not only cancer occurrence but also induction of inflammation of epithelial cells (Lyons et al., Cancer Res. 68; 4525-4530, 2008; Du et al., Cancer Res. 70:10080-10089, 2010). Thus, a compound which inhibits the function of Axin and further inhibits Snail expression by binding to GSK-3 may be usefully used for inhibiting inflammation by *Helicobacter* and gastric cancer occurrence.

On the other hand, niclosamide is an FDA-approved anthelmintic and has been widely used for infection by intestinal tapeworms for almost 50 years. Since it has been reported that niclosamide is an effective material of human colorectal cancer in vivo experiment or in vitro experiment (Osada T, et al., Cancer Res. 71:4172-4182, 2011; 13. Sack U, et al., J Natl Cancer Inst. 103:1018-1036, 2011), in recent researches, it has been reported that niclosamide can be used for various types of human cancer (Li Y, Li P K, Roberts M J, Cancer Lett., 349:8-14, 2014; Wang Y C et al., PLoS One. 8:e74538, 2013).

Niclosamide causes the death of cancer cells at a micromole concentration level in vitro experiment. On the other hand, the physiological concentration in vivo is nM level in serum and cancer tissues and shows non-toxic MoA (mode of action) in vivo experiment. Various targets such as Notch signal, Dishevelled, S100A4, and Frizzled receptor are suggested, but a direct target providing MoA (mode of action) of niclosamide has not been discovered yet.

In the present disclosure, as a result of efforts to find a therapeutic method of Axin-GSK3 interaction-related diseases such as familial adenomatosis polyposis (FAP) and *Helicobacter* infection, it has been confirmed that adenoma formation is inhibited in APC-MIN animal model to which niclosamide is orally administered, thereby completing the present disclosure.

SUMMARY

An object of the present invention is to provide a pharmaceutical composition for treating an Axin-GSK3 interaction-related disease.

To achieve the above object, the present invention provides a pharmaceutical composition for treatment or prevention of an Axin-GSK3 interaction-related disease comprising niclosamide or its pharmaceutically acceptable salt as an active ingredient.

The present invention also provides a method for treatment or prevention of an Axin-GSK3 interaction-related disease comprising administering niclosamide or its pharmaceutically acceptable salt.

The present invention also provides a use of niclosamide or its pharmaceutically acceptable salt for treatment or prevention of an Axin-GSK3 interaction-related disease.

The present invention also provides a use of niclosamide or its pharmaceutically acceptable salt for the preparation of medicine for treatment or prevention of an Axin-GSK3 interaction-related disease.

DETAILED DESCRIPTION

Figure 1A:
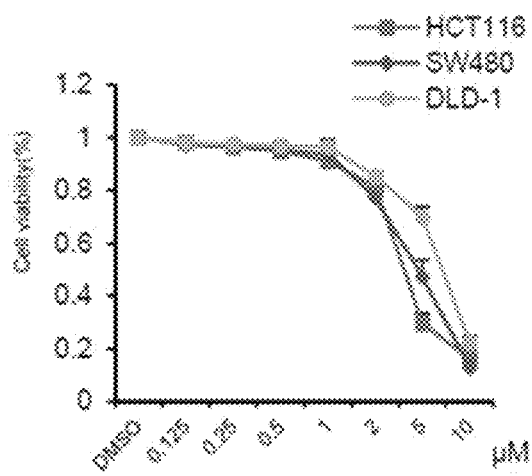
FIGS. 1A and 1B show the result of confirming the effect of treatment of niclosamide on colon cancer cells, and A shows the viability of colon cancer cells according to the treatment of niclosamide by concentration, and B shows the beta-catenin expression (left) and TCF/LEF transcriptional activity (right).

Unless otherwise defined, all technical and scientific terms used herein have the same meaning as commonly understood by those skilled in the art. In general, the nomenclature used herein is well known and commonly used in the art.

Herein, it was confirmed that niclosamide directly inhibited Axin-GSK3 complex formation in cells and recovered Snail-mediated epithelial-mesenchymal transition (EMT) and weakened Wnt activity. In addition, it was confirmed that niclosamide inhibited the activation of transcriptional activity of TCF/LEF induced in APC mutant which was confirmed in FAP patients. Furthermore, it was confirmed that the adenoma formation was inhibited, when niclosamide was orally administered in the APC-MIN model which was established to form adenoma in colon.

Thus, the present invention relates to a pharmaceutical composition for treatment or prevention of Axin-GSK3 interaction-related disease comprising niclosamide or its pharmaceutically acceptable salt as an active ingredient.

Niclosamide (or Niclocide (trade name)) is a drug which has been used for almost 50 years as an anthelminthic, and it has been known to have the anti-tumor activity potentially, and it is an orally available drug.

Niclosamide has been recently suggested to be capable of functioning as an anticancer drug which controls several signal pathways such as Wnt, S100A4, Notch and androgen receptors, although its molecular target is not clearly discovered (Osada T, et al. Cancer Res. 71:4172-4182, 2011; Sack U, et al. J Natl Cancer Inst. 2011; 103(13):1018-1036, 2011; Li Y, et al., Cancer Lett. 349:8-14, 2014).

Familial adenomatosis polyposis (FAP) is occurred by defects of APC (adenomatous polyposis coli), and FAP patients have hundreds of adenomatous polyps in the intestine at an early age, and ultimately, 100% colorectal adenocarcinoma progresses (Minde D P et al., Mol Cancer. 2011; 10:101, 2011; Half E et al., Orphanet J Rare Dis., 4: 22, 2009). US FDA and European health groups have approved anti-inflammatory drugs as some additional therapies, but the therapeutic effect is insignificant.

The oral administration of niclosamide according to the present invention will be effective as a new drug which treats FAP.

In one aspect of the present invention, as the result of administering niclosamide to the APC-Min mouse model having the same genetic background and symptoms as FAP patients, in case of the mouse to which niclosamide was intraperitoneally administered, at 14 weeks, the intestinal adenoma was significantly reduced. On the other hand, there was no change in body weight. In the APC-MIN model to which niclosamide was orally administered for 14 weeks, the intestinal adenoma formation was significantly inhibited and the experimental animal was stable during the drug treatment.

Through this result, it can be seen that niclosamide can be used as a new therapeutic agent for FAP patients.

In addition, herein, the result of inhibiting inflammation by *Helicobacter* infection and gastric cancer progression is suggested, and this result indicates that it can be effectively used for various inflammatory diseases caused by GSK-3 activity reduction.

Herein, it was confirmed that niclosamide inhibited that Axin and GSK3 bound to form a complex and thereby weakened Wnt activity and recovered Snail-mediated EMT in colorectal cancer cells. In addition, the clinical validity of niclosamide as a potential therapy for FAP patients was provided.

Figure 1B:
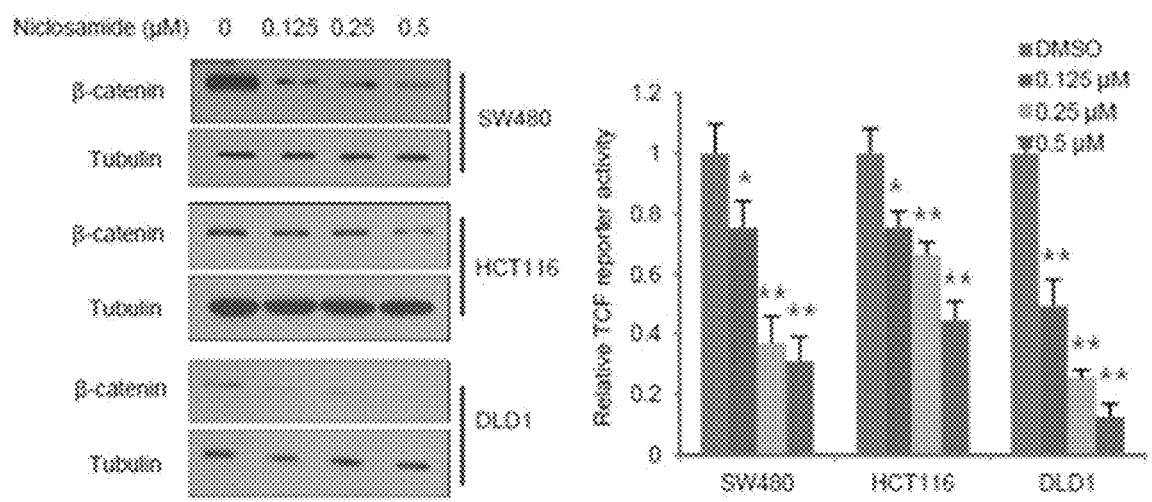

In another aspect of the present invention, whether niclosamide induced apoptosis of colorectal cancer cells was confirmed, and as shown in A of FIG. 1, it was confirmed that niclosamide induced death of colorectal cancer cells at a μM concentration level, and on the other hand, it was confirmed that apoptosis did not occur at a nM concentration.

Herein, it was confirmed that niclosamide was used at a nM concentration and the colon adenoma was inhibited through a mechanism other than cancer cell death.

Herein, as a molecular target of niclosamide, GSK3-Axin2 interaction was confirmed. Niclosamide recovered Snail-mediated EMT in cancer cells, and thereby a new MoA inhibiting Wnt activity was provided.

Thus, niclosamide of the present invention can be used for treatment or prevention of Axin-GSK3 interaction-related disease, and the Axin-GSK3 interaction-related disease may be familial adenomatosis polyposis (FAP), adenomatous colitis, adenomatous colorectal cancer, Alzheimer, diabetes, rheumatoid arthritis, inflammatory skin disease, osteoarthritis, leukopenia and the like.

Thus, in other aspect, the present invention relates to a method for treatment or prevention of Axin-GSK3 interaction-related disease comprising a step of administering niclosamide or its pharmaceutically acceptable salt.

In other aspect, the present invention relates to a use of niclosamide or its pharmaceutically acceptable salt for treatment or prevention of Axin-GSK3 interaction-related disease.

In other aspect, the present invention relates to a use of niclosamide or its pharmaceutically acceptable salt for preparation of medicine for treatment or prevention of Axin-GSK3 interaction-related disease.

Herein, in addition, the abnormality of Wnt signal pathway is related to many diseases including cancer, bone metabolism, degenerative disease and fibrosis, and despite of targets of Wnt therapy such as Frizzled receptor, Porcupine, Dishevelled, p300 and CBP, an effective molecular target which controls Wnt pathway has not been discovered yet.

Herein, during Wnt activation, APC-Axin-Dishevelled scaffolding complex controls TCF/LEF activity. It was confirmed that inhibition of Axin-GSK3 interaction could be a new target capable of weakening Wnt activity and recovering Snail-mediated EMT program.

A carrier used for the pharmaceutical composition of the present invention includes pharmaceutically acceptable carriers, adjuvants, and vehicles, and it is collectively referred to as "a pharmaceutically acceptable carrier". The pharmaceutically acceptable carrier which can be used for the pharmaceutical composition of the present invention includes ion exchange, alumina, aluminum stearate, lecithin, serum protein (e.g. human serum albumin), buffer material (e.g. various phosphates, glycine, sorbic acid, potassium sorbate, partial glyceride mixture of saturated vegetable fatty acid), water, salt or electrolyte (e.g. protamine sulfate, disodium hydrogen phosphate, potassium hydrogen phosphate, sodium chloride and zinc salt), colloidal silica, magnesium trisilicate, polyvinyl pyrrolidone, cellulose-based substrate, polyethylene glycol, sodium carboxymethylcellulose, polyacrylate, wax, polyethylene-polyoxypropylene-block polymer, polyethylene glycol and wool fat and the like, but not limited thereto.

The administration route of the medical composition according to the present invention includes oral, intravenous, intramuscular, intra-arterial, intramedullary, intradural, intracardiac, percutaneous, subcutaneous, intraperitoneal, intranasal, intestinal, local, subglossal, or rectal administration, but not limited thereto.

Oral and parenteral administration is preferable. The term used herein, "parenteral" includes subcutaneous, intradermal, intravenous, intramuscular, intra-articular, intrabursal, intrasternal, intradural, intralesional and intracranial injection or infusion techniques.

The pharmaceutical composition may be a form of sterile injection preparation as a sterile injectable aqueous or oily suspension. This suspension may be formulated using a suitable dispersing agent or wetting agent (e.g. Tween 80) and suspending agent according to the techniques known in the art. The sterile injectable preparation also may be a sterile injectable solution or suspension in non-toxic parenterally acceptable diluent or solvent (e.g. solution in 1,3-butanediol). The acceptably usable vehicle and solvent include mannitol, water, Ringer's solution, and isotonic sodium chloride solution. In addition, sterile non-volatile oil is commonly used as the solvent or suspending medium. For this object, any non-volatile oil having little magnetic polarity including synthetic mono- or di-glyceride may be used. Fatty acids such as oleic acid and its glyceride derivatives are useful for injection preparations as same as pharmaceutically acceptable natural oil (e.g. olive oil or castor oil), in particular, those polyoxyethylated.

The pharmaceutical composition of the present invention may be orally administered in any orally acceptable capacity form, including capsules, tablets, and aqueous suspension and solution, but not limited thereto. In case of oral tablets, the commonly used carrier includes lactose and corn starch. A lubricant such as magnesium stearate is also typically added. In case of oral administration in a capsule form, useful diluents include lactose and dried corn starch. When the aqueous suspension is orally administered, the active ingredient is mixed with an emulsifying agent and a suspending agent. If necessary, a sweetening agent and/or a flavoring agent and/or a coloring agent may be added.

The pharmaceutical composition of the present invention may be also administered in a form of suppository for rectal administration. This composition may be prepared by mixing the compound of the present invention with a suitable non-magnetic excipient which is solid at room temperature but is liquid at a rectal temperature. Such material includes cocoa butter, wax and polyethylene glycol, but not limited thereto.

The oral administration of the pharmaceutical composition according to the present invention is particularly useful when the targeted treatment is associated with a site or organ that is accessible by local application. When applying to skin locally, the pharmaceutical composition should be formulated as a suitable ointment containing an active ingredient suspended or dissolved in a carrier. The carrier to administer the compound of the present invention locally includes mineral oil, liquid paraffin, white petrolatum, propylene glycol, polyoxyethylene, polyoxypropylene compound, oil wax and water, but not limited thereto. As other way, the pharmaceutical composition may be formulated as a suitable lotion or cream containing an active compound suspended or dissolved in a carrier. The suitable carrier includes mineral oil, sorbitan monostearate, polysorbate 60, cetyl ester wax, cetearyl alcohol, 2-octyldodecanol, benzyl alcohol, and water, but not limited thereto. The pharmaceutical composition of the present invention may be also locally applied through lower intestine with rectal suppository, as well as a suitable enema. A locally applied transdermal patch is also included in the present invention.

The pharmaceutical composition of the present invention may be administered by intranasal aerosol or inhalation. Such a composition may be prepared according to techniques known well in the art of medicine, and it may be prepared as a solution in saline using benzyl alcohol or other suitable preservatives, sorbefacients for enhancing bioavailability, fluorocarbon and/or other solubilizers or dispersing agents known in the art.

The compound of the present invention may be used as mixed with a common anti-inflammatory agent, or mixed with a matrix metalloprotease inhibitor, a lipoxygenase inhibitor and an inhibitor cytokine other than IL-1β. The compound of the present invention may be administered as mixed with an immunomodulator (e.g., bropirimine, anti-human alpha interferon antibody, IL-2, GM-CSF, methionine enkephalin, interferon alpha, diethyldithiocarbamate, tumor necrosis factor, naltrexone and rEPO) or prostaglandin, in order to prevent or eradicate IL-1 mediated disease symptoms such as inflammation. When the compound of the present invention is administered as mixed with other therapeutic agent, they may be administered to a patient sequentially or simultaneously.

The term "therapeutically effective dose" indicates a dosage level of about 1 mg to about 100 mg per kg body weight per day for use in the treatment of the above symptoms in humans (typically about 60 mg to about 6 g/patient/day).

The term "prophylactically effective dose" indicates a dosage level of about 0.1 mg to about 100 mg per kg body weight per day for use in the prevention of the above symptoms in humans (typically about 6 mg to about 6 g/patient/day).

However, it should be understood that a specific effective dose for a specific patient may be variable depending on various factors including activity of the used specific compound, age, body weight, general health, gender, prescribed diet, administration time, administration route, emission rate, drug mix and severity of the specific disease to be prevented or treated. The medical composition according to the present invention may be formulated as tablets, sugar-coated tablets, capsules, liquid, gel, syrup, slurry, and suspension.

When the medical composition according to the present invention is administered to subcutaneous cells of fish, it may be administered to a branchial pouch or digestive tract. Injection may be injected to muscle cells in muscle tissue or other cells, and it may be injected to visceral cells in the abdominal cavity.

As a preferred aspect, the medical composition for oral administration may be prepared by mixing an active ingredient with a solid excipient, and it may be prepared in a form of granules so as to prepare it in a form of tablets or sugarcoated tablets. As a suitable excipient, a filler of carbohydrates such as a sugar form like lactose, sucrose, mannitol and sorbitol, or starch from corn, wheat flour, rice, potatoes or other plants, cellulose like methylcellulose, hydroxypropyl methyl-cellulose or sodium carboxymethyl-cellulose, gum including Arabic gum, tragacanth gum, or protein such as gelatin and collagen may be used. If needed, a disintegrating agent or solvent in each salt form such as cross-linked polyvinyl pyrrolidone, agar and alginic acid or sodium alginate may be added.

As a preferred aspect, in case of parenteral administration, the medical composition of the present invention may be prepared as an aqueous solution. Preferably, a physically appropriate buffer solution such as Hank's solution, Ringer's solution or a physically buffered saline may be used. For aqueous injection suspension, a substrate, which can increase the viscosity of suspension, like sodium carboxymethyl cellulose, sorbitol or dextran may be added. In addition, the suspension of the active ingredient may be prepared as a suitable oily injection suspension. A suitable lipophilic solvent or carrier includes fatty acids such as sesame oil, or synthetic fatty acid ester such as ethyl oleate, triglyceride or liposome. Polycationic amino polymers may be used as a carrier. Optionally, the suspension may use a suitable stabilizer or agent to increase the solubility of the compound and to prepare a high concentration of solution.

EXAMPLES

Hereinafter, the present I invention will be described in more detail by examples. These examples are intended only to illustrate the present invention more specifically, and it should be obvious to those skilled in the art that the scope of the present invention is not limited by these examples according to the gist of the present invention.

Example 1: Analysis of Apoptosis Activity of Colorectal Cancer Cells by Niclosamide In order to confirm whether niclosamide induced apoptosis of colorectal cells, the effect on viability and mobility were confirmed.

$1 \times 10^5$ cells of colorectal cancer cell lines HCT116, SW480 and DLD-1 cell (ATCC, American Type Culture Collection) were cultured overnight in a 6-well plate, and then were washed with PBS, and were cultured in a culture medium treated with niclosamide by each concentration (0 μM, 0.125 μM, 0.25 μM, 0.5 μM, 1 μM, 2 μM, 5 μM and 10 μM) for 48 hours. Apoptosis was measured with trypan blue assay and cell viability was calculated by an equation [1−(number of dead cells/total number of cells)].

As a result, as shown in A of FIG. 1, it was confirmed that niclosamide induced death of colorectal cells at a μM concentration level, and on the other hand, it was confirmed that apoptosis did not occur at a nM concentration.

Example 2: Confirmation of Snail-Mediated EMT Recovery Activity of Colorectal Cancer Cells by Niclosamide In order to confirm whether niclosamide induced snail-mediated EMT recovery, beta-catenin (β-catenin) expression and TCF/LEF reporter (Topflash) activity change, and Snail and E-cadherin protein expression were confirmed.

At first, after treating niclosamide of nM units at concentrations of 0 nM, 0.125 nM, 0.25 nM and 0.5 nM to colorectal cancer cells for 24 hours, the beta-catenin (β-catenin) activity and TCF/LEF reporter (Topflash) activity of colorectal cancer cells were measured.

For beta-catenin, western blot was performed using β-catenin (#610154, BD Transduction, 1:5,000) antibody, and as a result, as shown in B (left) of FIG. 1, expression of beta-catenin in colorectal cancer cells was reduced as the concentration of treated niclosamide was increased.

The TCF/LEF transcriptional activity was carried out by transformation with 100 ng of a reporter gene and 1 ng of transfection control pRL-SV40-Renilla. The reporter activity was measured with a dual luciferase assay system (Promega) in 48 hours after infection, and was standardized by measuring the co-transformed renilla activity, and the reporter gene activity was represented by light units in proportion to light units obtained from the negative control group.

As a result, as shown in B (right) of FIG. 1, the TCF/LEF transcriptional activity was reduced as the concentration of treated niclosamide was increased.

Figure 2A:
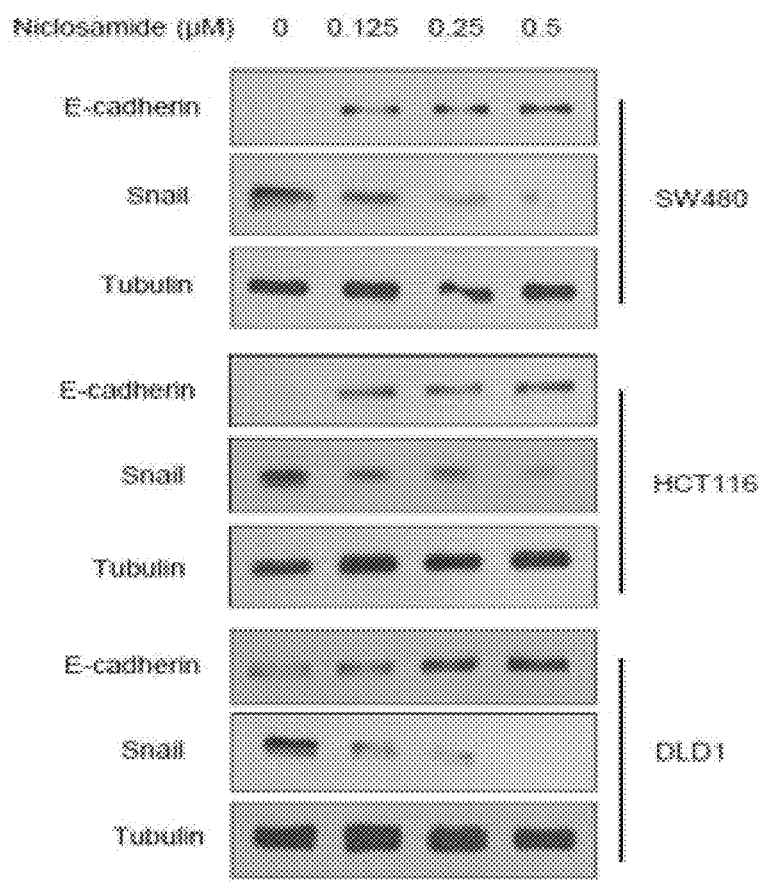
FIGS. 2A and 2B show the change of expression of Snail (A) and the change of E-cadherin activity (B) according to the treatment of niclosamide.
Figure 2B:
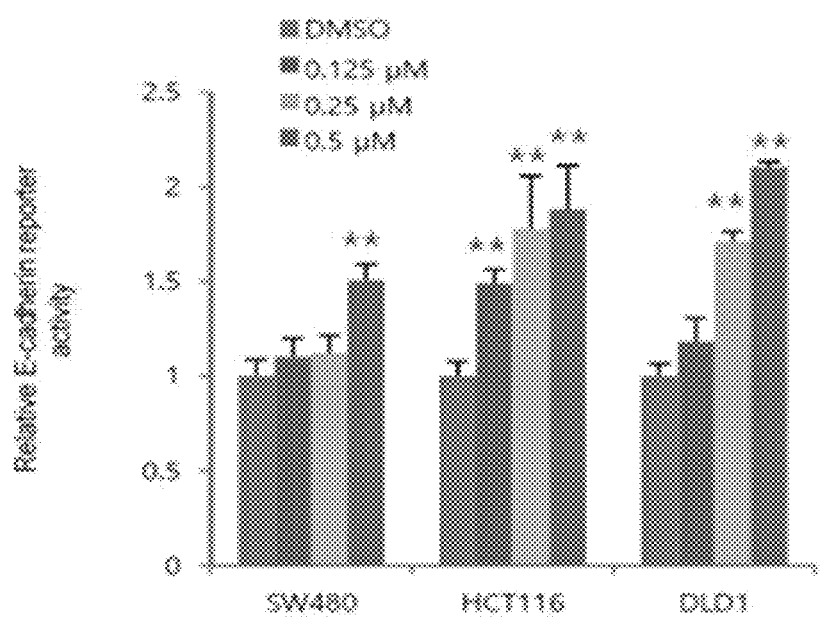

Through the western blot, Snail expression change was confirmed, and through the dual luciferase assay system, the expression of E-cadherin protein was confirmed. As a result, as shown in FIG. 2A, the expression of Snail was reduced as the concentration of treated niclosamide was increased, but on the other hand, as shown in FIG. 2B, E-cadherin was increased.

It was judged that Snail functioning as an E-cadherin transcription inhibitor was reduced by niclosamide treatment, and thereby the E-cadherin promoter activity in colorectal cells was increased.

Example 3: Confirmation of Inhibition of Axin2 Function in Colorectal Cancer Cells of Niclosamide In order to confirm whether niclosamide inhibited Axin2 function in colorectal cancer cells, the change of the GSK3 amount in cell nuclei was confirmed.

After treating niclosamide of 0.25 nM to colorectal cancer cell lines HCT116, SW480 and DLD-1 cells for 24 hours, the amount of GSK3, β-catenin and Snail of nucleo-cytoplasm fractions was analyzed by immunoblotting.

The amount of Snail and GSK3 protein in cells was confirmed by separating nuclei and cytoplasm in the hypotonic solution (Kim N H, et al., Sci Signal. 4:ra71, 2011; Yook J I, et al. Nat Cell Biol., 8:1398-140, 2006). Briefly, after collecting colorectal cancer cells ($1 \times 10^6$ cells) in a centrifugation tube, they were washed with PBS and were treated with the hypotonic solution (10 mM HEPES, pH7.9; 10 mM KCl; 1 mM DTT with protease inhibitors) 400 µl on ice for 5 minutes. The cell membrane was degraded by addition of 10% NP-40, and the final concentration was adjusted to 0.6% final concentration, and then was mixed well and high-speed centrifugation was conducted for 30 seconds. The cytoplasmic resolvents were separated and nuclear precipitates were washed with cold PBS twice. The nucleoprotein was extracted by treating hypertonic buffer (20 mM HEPES, pH7.9; 0.4 M NaCl; 1 mM DTT with protease inhibitors) on ice for 15 minutes, and then high-speed centrifugation was conducted, and the amount of GSK3, β-catenin and Snail of nucleo-cytoplasm fractions was analyzed by immunoblotting.

Figure 3:
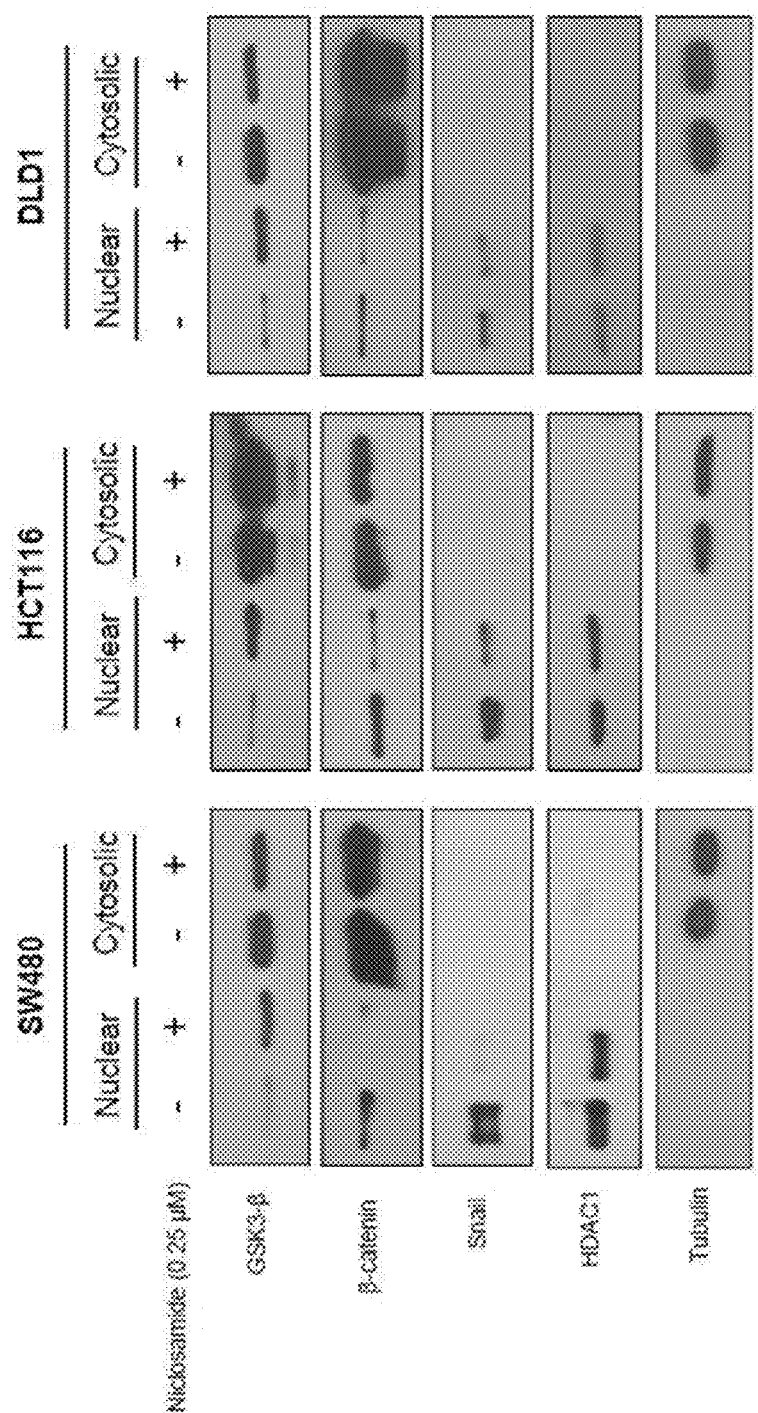
FIG. 3 shows the result of analyzing the amount of GSK3, β-catenin, and Snail in nucleo-cytoplasm fractions of colon cancer cells according to the treatment of niclosamide.

As a result, as shown in FIG. 3, it was confirmed that GSK3 of nuclei was increased and the amount of beta-catenin and Snail was reduced, by niclosamide treatment.

The above result shows that niclosamide can control Axin function in colorectal cancer cells.

Example 4: Confirmation of Inhibitory Ability of Axin-GSK3 Complex Formation of Niclosamide In order to confirm whether niclosamide could inhibit Axin-GSK3 interaction, to perform an immunoprecipitation experiment under the condition with or without niclosamide, cell lysates having full-length Axin2 were investigated.

The immunoprecipitation assay was performed as follows (Yook J I, et al. Nat Cell Biol. 8:1398-1406, 2006).

The doxycycline-induced His-tagged Axin2 expression vector was transformed to MCF-7 cell (ATCC, American Type Culture Collection) and was cultured, and was reacted by treating Ni—Ti beads (Invitrogen) and niclosamide of each concentration to Triton X-100 lysates of total cells. The protein recovered in beads was subjected to SDS-PAGE, followed by immunoblot analysis, and a control group of 1/20 volume was added.

Figure 4A:
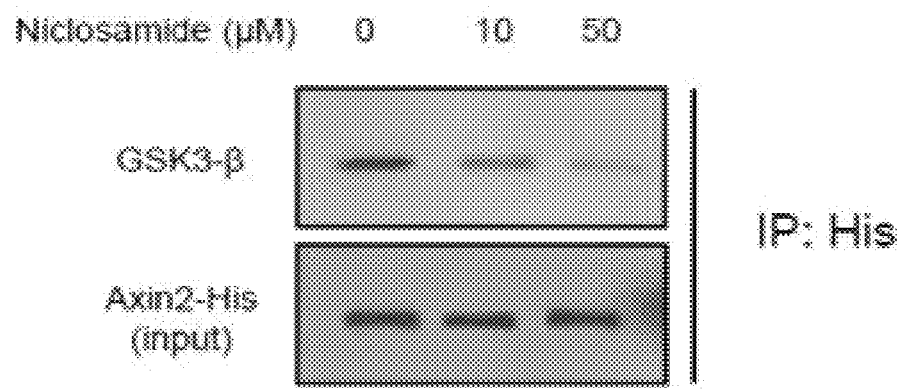
FIGS. 4A and 4B show the result of confirming whether the formation of Axin-GSK3 complexes is inhibited by niclosamide.

As a result, as shown in FIG. 4A, it was confirmed that niclosamide reduced GSK3 which bound to Axin2 in total cell lysates.

Since it was disclosed that the hydrophobic residues of alpha helix of Axin were accumulated to the hydrophobic groove formed by the C-terminal loop of GSK3, in the result of structural analysis of Axin-GSK3 binding announced in the past (Dajani R et al., EMBO J. 22:494-501, 2003), the present inventors hypothesized that niclosamide binds to the hydrophobic groove of GSK3 and interferes with the function of Axin, and in order to confirm it, they designed in vitro analysis to confirm competitive inhibition by niclosamide of recombinant GSK3 which binds to a 19-mer FITC-linked Axin peptide.

His-tagged recombinant GSK3 beta was obtained from sf9 insect cells by the known method (Lee D G, et al. Nat Commun. 5:4423, 2014). The FITC-linked 19-mer Axin peptide known to bind to GSK3 as amphipathic alpha-helix (Axin1, 383-401, VEPQKFAEELIHRLEAVQR) was chemically synthesized (Peptron). In order to confirm competitive binding of the synthesized Axin peptide and niclosamide, His-tagged recombinant GSK3 and Ni—Ti beads were treated with niclosamide for 2 hours, and were washed with PBS 3 times and then quantitative fluorometry was performed using Ni—Ti beads. The fluorescence strength was shown in proportion to the fluorescence strength obtained in the negative control group from 3 times of experiments.

Figure 4B:
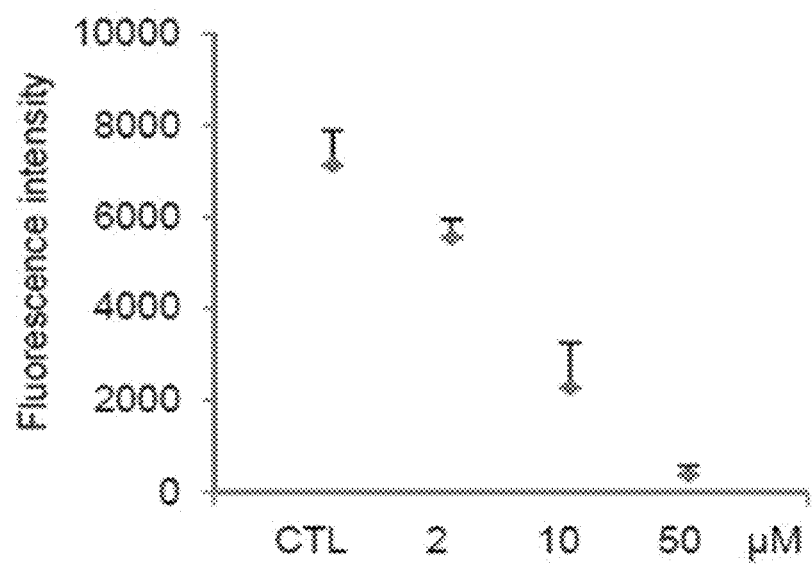

As a result, it was confirmed that the interaction between the recombinant GSK3 and synthesized Axin peptide was inhibited in proportion to the administration concentration of niclosamide (FIG. 4B).

In order to confirm whether niclosamide directly binds to GSK3, surface plasma resonance (SPR) analysis was conducted.

SPR was carried out using ProteOn™ XPR36 Protein Interaction Array system (Bio-Rad Laboratories, Inc., CA, USA), and the purified recombinant GSK3 beta was immobilized on ProteOn GLH sensor chip. The niclosamide or 19-mer wild-type Axin peptide or mutant peptide (VEPQ-KAAEEAIHRAEAVQR, mutation underlined) was diluted with phosphate-buffered saline+Tween 20+1% DMSO at different concentrations respectively, and then was flowed into the chip at a rate of 100 µl/min, and the result was analyzed by ProteOn Manager Software 2.0 using the standard Langmuir models for fitting kinetic data. The complex formation ratio was represented by an association constant (ka, in the unit of M−1s−1), and the complex decrement ratio was represented by a dissociation constant (kd, in the unit of s−1) as the following equilibrium equation 1.

$$A + B \underset{kd}{\overset{ka}{\rightleftharpoons}} AB \qquad (1)$$

The high-affinity interaction is represented by the low dissociation constant, and gradual cognition and binding with interactant (rapid "on rate," or high ka), and stability of complex formation (slow "off rate," or low kd) are equal to the equation KD=kd/ka.

Figure 5A:
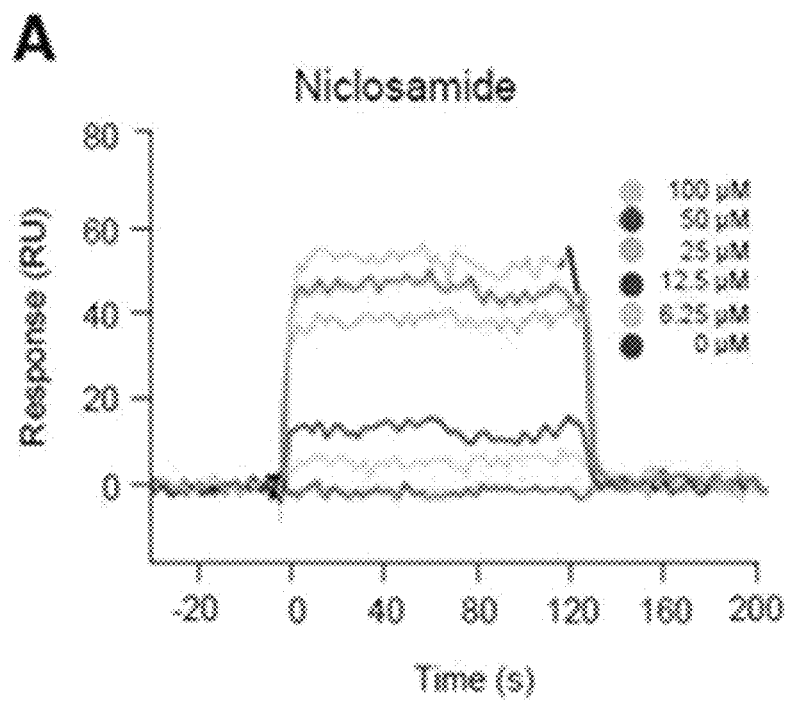
FIGS. 5A and 5B show the result of surface plasma resonance (SPR) analysis for confirming whether niclosamide directly binds to GSK3.
Figure 5B:
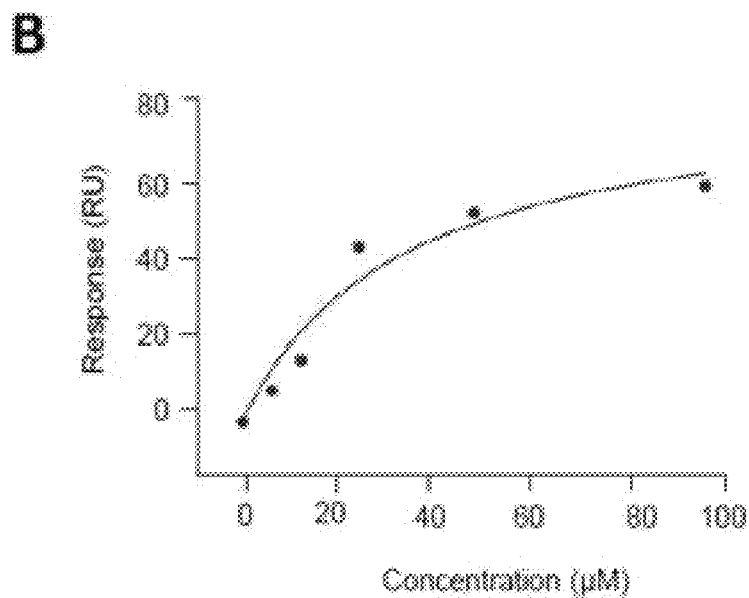

As a result, as shown in FIGS. 5A and B, the wild-type Axin peptide and niclosamide directly bound to GSK3. Equilibrium dissociation constants, KD values, were 35 µM and 34 µM, respectively, in the SPR analysis. The mutant Axin peptide having a mutation in the hydrophobic residue immobilizing on GSK3 protein on the sensor surface could not bind up to 100 micromoles.

In addition, in order to structurally analyze the interaction of Axin binding portion of GSK3 and niclosamide, molecular docking analysis was performed.

The molecular docking measurement was carried out using Maestro 10.4 molecular docking suite. The crystal structure of human (pTyr216)-GSK3β to which the Axin peptide was attached was measured with RCSB Protein Data Bank (PDB ID: 3ZDI). All water molecules and metal ions were removed and hydrogen atoms were added to the protein, and to add protons to the physiological pH to the ligand different from the sample, Epik module was used. All compounds were docked to the receptor structure by minimizing energy and using standard precision (SP) module of the Glide docking module within the Schrodinger Suite. Before Glide docking analysis, a receptor grid box was produced in the center of the co-crystal ligand. To optimize the geometric shape, post-minimization was performed.

Figure 5C:
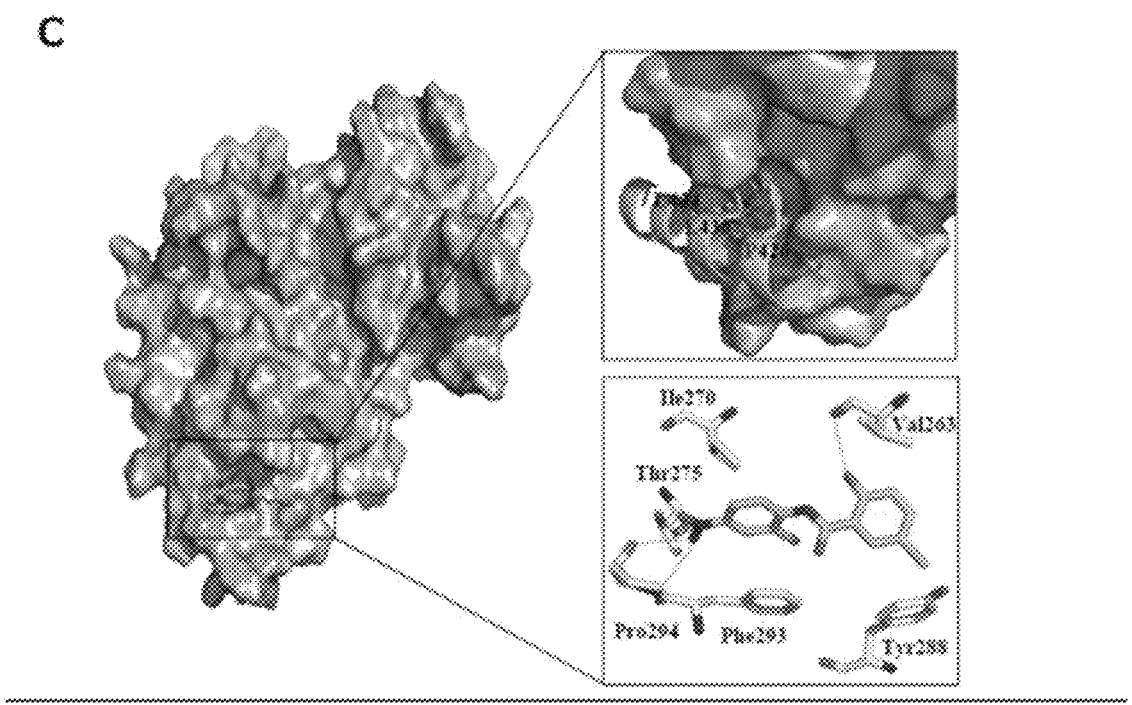
FIG. 5C shows the result of structural analysis of Axin binding part of GSK3 and niclosamide.

As a result, as shown in FIG. 5C, 1-chloro-3-nitrobenzene group of niclosamide entered the hydrophobic hole formed from Val 263, Leu 266, Val 267 and Ile 270 residues of human GSK3 beta, and was accumulated on the Phe 293 residue through π-π interaction. Niclosamide formed hydrogen bonds with Pro294, Thr275 and Val 263 additionally, and bound to Tyr288 and halogen on the Axin-GSK3 surface. Thus, it was confirmed that niclosamide interrupted the Axin-GSK3 complex by inhibiting protein-protein interaction (PPI).

Example 5: Confirmation of Restoration Ability of Epithelial-Mesenchymal Transition (EMT) of Niclosamide The epithelial-mesenchymal transition (EMT) by Snail increases the potential of cell movement and tumor formation. In order to confirm the epithelial-mesenchymal transition (EMT) restoration ability of niclosamide, the effect on mobility of colorectal cancer cells and tumor formation of colorectal cancer cells of niclosamide was confirmed.

At first, the effect on the cell mobility of colorectal cancer cells of niclosamide was confirmed. Colorectal cancer cell lines HCT116, SW480 and DLD-1 cells were cultured under the condition with or without niclosamide for 48 hours, and then the upper part of the membrane was rubbed with a cotton swab and the number of movements of cells inserted into the basement membrane was stained with 0.25% crystal violet and counted. Cells were counted in five random fields.

Figure 6A:
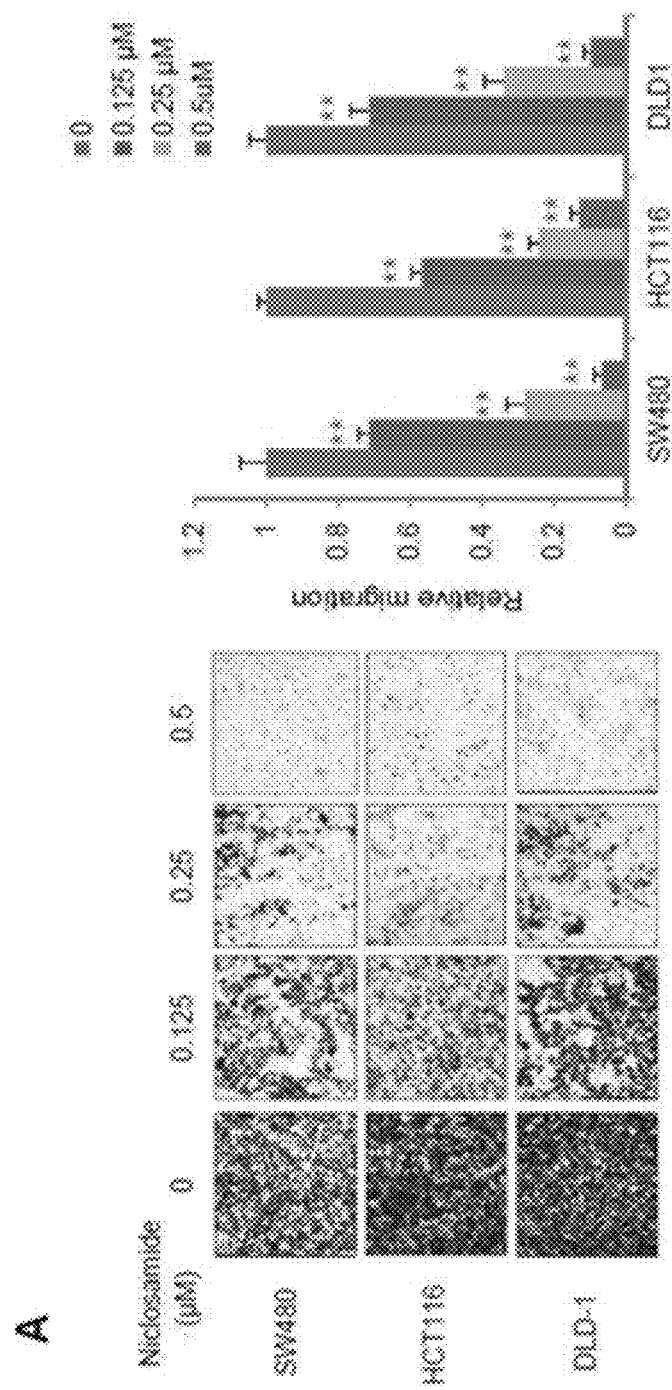
FIGS. 6A and 6B show the cell migration ability (A) of colon cancer cells treated by niclosamide and the result of tumor formation change (B) by niclosamide in the mouse to which colon cancer cells are administered, for confirming the epithelial-mesenchymal transition (EMT) restoration ability of niclosamide.

As a result, when niclosamide was treated at a nM level, the potential of movements of colorectal cancer cells was largely reduced (FIG. 6A).

Next, the effect of niclosamide having tumor formation potential in vivo experiment of HCT116 and SW480 cells was investigated.

Colorectal cancer cell lines HCT116 ($5 \times 10^6$ cells) and SW480 ($5 \times 10^6$ cells) were mixed in 100 μl PBS and were injected into flank subcutaneous tissues in female athymic nude mice (6 weeks old). Mice were randomly assigned to two groups and a vehicle and niclosamide were intraperitoneally injected daily and they were treated for 24 hours. Niclosamide was dissolved with 10% Cremophor EL (BASF) and 0.9% NaCl and then was intraperitoneally injected. After injection of colorectal cancer cells, mice were observed daily and the weight change was measured twice a week. In addition, when a tumor was observed, it was measured with calipers. The tumor size was calculated by the equation (LXW2)/2. Herein, L is a long diameter of the tumor and W is a short diameter.

Figure 6B:
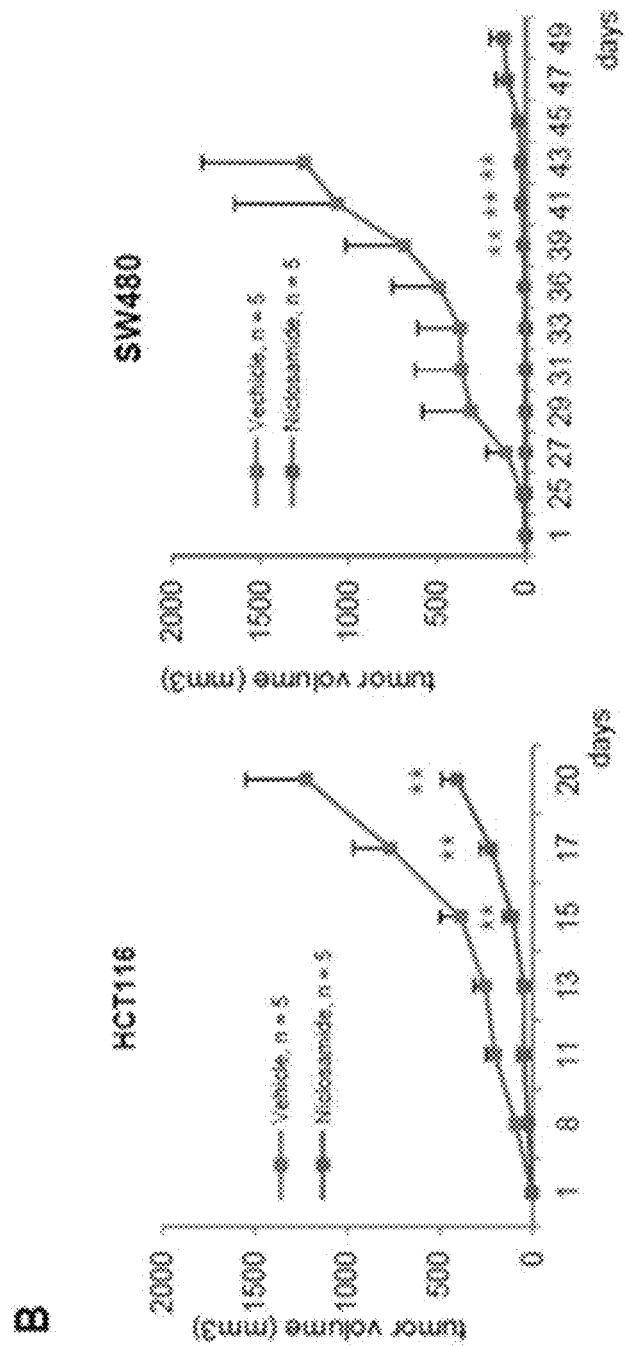

As a result, as shown in FIG. 6B, the intraperitoneal administration of niclosamide significantly inhibited the tumor growth of colorectal cancer cells in vivo experiment (FIG. 6B).

In order to investigate in vivo MoA of niclosamide controlling Snail-mediated EMT, through xenografts, the change of protein amount of Snail and E-cadherin in the tumor by niclosamide treatment was confirmed.

The colorectal cancer cell line, SW480 cells ($5 \times 10^6$) were subcutaneously injected to nude mice. When the tumor size became 500 mm$^3$ on average, mice were randomly divided into 3 groups, and a vehicle or niclosamide (50 mg/kg, 200 mg/kg) was intraperitoneally injected for 3 days. After sacrificing mice, the tumor tissue part was separated using Pro-prep protein extraction solution (#17081, Intron), and the amount of protein of Snail and E-cadherin in the tumor sample was measured by immunoblot assay.

Figure 7:
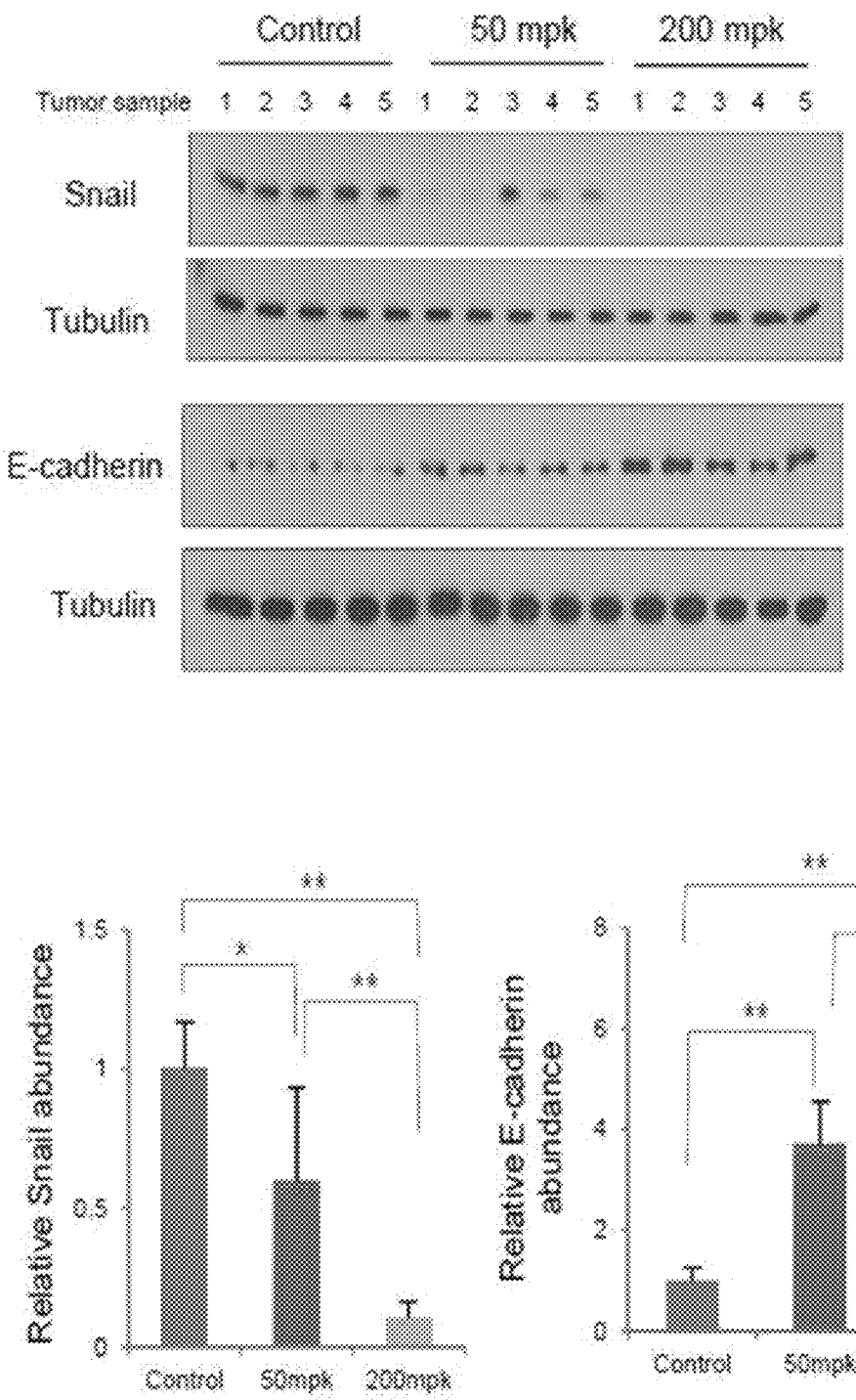
FIG. 7 shows the result of measuring the change of the amount of protein of Snail and E-cadherin by niclosamide treatment with immunoblot assay in the heterologous tumor transplantation.

As a result, as shown in FIG. 7, in vivo experiment, the presence of Snail was reduced, but on the other hand, the amount of E-cadherin was increased, as the concentration of treated niclosamide increased.

From the above results, it could be seen that niclosamide inhibited the tumor formation potential by restoring Snail-mediated EMT.

Example 6: Confirmation of Inhibitory Ability of Adenoma Formation by Niclosamide The effect of niclosamide on the treatment of adenomatous colorectal cancer and familial adenomatosis polyposis (FAP) occurred by mutation of APC gene was confirmed.

Based on the results of Examples 2-5 that niclosamide inhibited Wnt activity and EMT through Axin-GSK3 inhibition, whether niclosamide could attenuate the TCF/LEF transcriptional activity induced by mutant APC was confirmed.

After transforming the mutant APC expression vector, pCMV-neo-Bam APC 1-1309 (#16508, Addgene) or pCMV-neo-BamAPC 1-1941 (#16510, Addgene) and Topflash reporter vector to 293 cell (ATCC), niclosamide (0 μM, 0.125 μM, 0.25 μM and 0.5 μM) was treated for 24 hours. The TCF/LEF transcriptional activity was quantified by measuring the luciferase activity as same as Example 2.

Figure 8A:
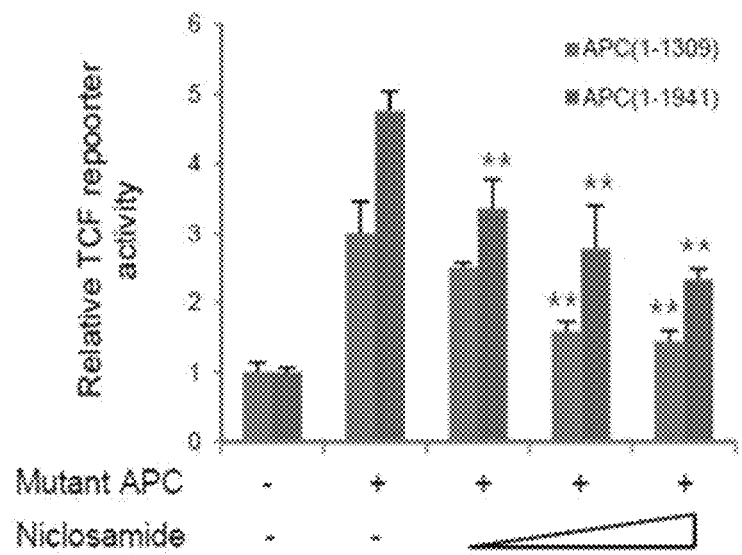
FIGS. 8A and 8B shows the result of confirming the change of TCF/LEF transcriptional activity by niclosamide in the 293 cell transformed by mutant APC.
Figure 8B:
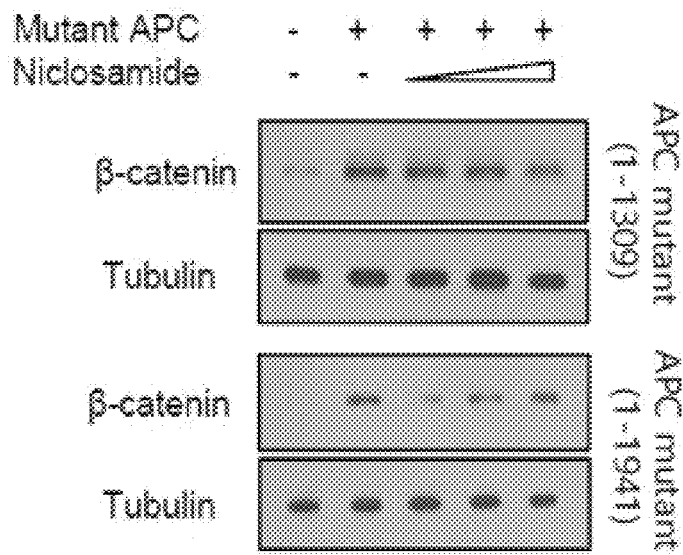

As a result, as shown in FIG. 8, when transforming mutant APC to the 293 cell, the TCF/LEF transcriptional activity was increased, and the increased transcriptional activity was reduced as the administration-concentration of niclosamide increased.

In addition, in order to confirm the therapeutic effect of niclosamide in vivo, the effect of niclosamide affecting on adenoma formation in APC-MIN (multiple intestinal neoplasia, APCΔ850) mice model was confirmed.

APC-MIN mice were prepared by crossbreeding of wild-type C57BL/6J (APC+/+) females and MIN C57BL/6J (APCMin/+) males, and APC-MIN descendants were randomly assigned in subgroups at 3 weeks age by identifying with PCR-based assay. A vehicle or niclosamide (50 mg/kg) was intraperitoneally injected daily (6 days/week), and mice were observed daily, and the weight was measured twice a week. After the end of 14 weeks, mice were sacrificed and the whole intestine was collected and intestinal flakes were opened longitudinally with scissors, and were washed with saline and were unfolded, and then tissues were obtained. The tissues were fixed with 10% formalin for 24 hours and were washed with 70% alcohol. The fixed intestinal tissues were observed using a stereomicroscope, and the size of adenoma (small, <1 mm; medium 1~3 mm; large >3 mm) was discriminated and counted for each mouse. In case of oral administration, APC-MIN mice ingested niclosamide mixed with 15% sugar gel vehicle daily (6 days/week) for 14 weeks. The number and size of adenoma were measured with a stereomicroscope.

Figure 9:
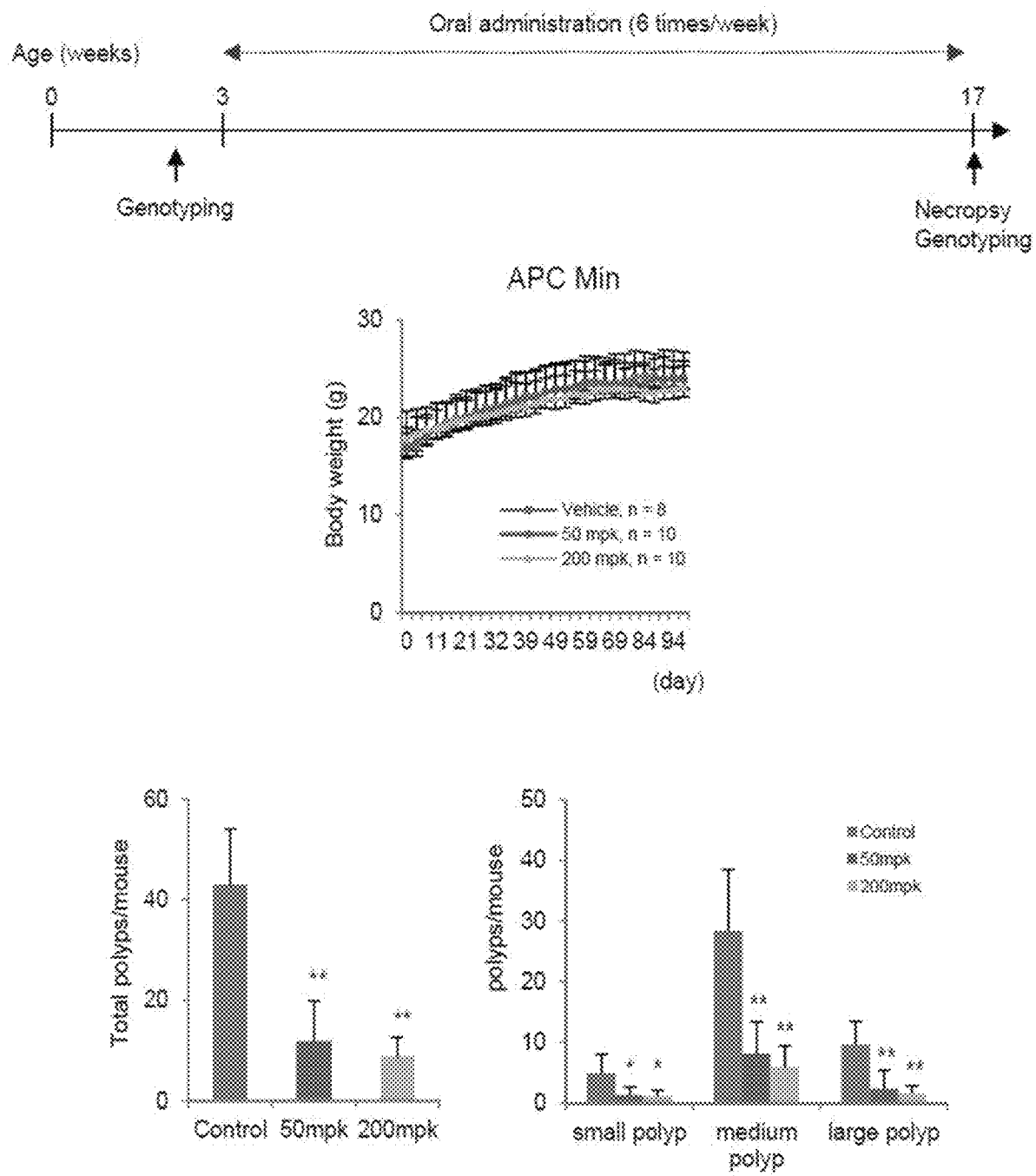
FIG. 9 shows the result of confirming the size change of adenoma when niclosamide is administered to APC-MIN animal model.

The result was shown in FIG. 9. In case of mice in which niclosamide was administered intraperitoneally, at 14 weeks, the intestinal adenoma was significantly reduced. On the other hand, the body weight did not change. In the APC-MIN model in which niclosamide was orally administered for 14 weeks, the intestinal adenoma formation was significantly inhibited, and the experimental animal was stable during the drug treatment.

Through this result, it could be seen that niclosamide could be used as a new therapeutic agent for FAP patients.

Example 7: Inhibition of *Helicobacter* Function by Niclosamide

Figure 10A:
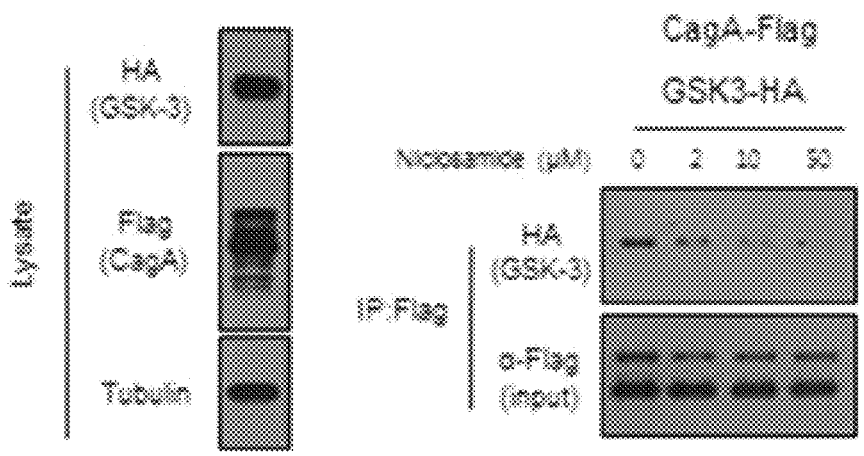
FIGS. 10A and 10B shows the result of inhibiting the binding between *Helicobacter* CagA and GSK-3 and inhibiting the Snail expression by niclosamide.
Figure 10B:
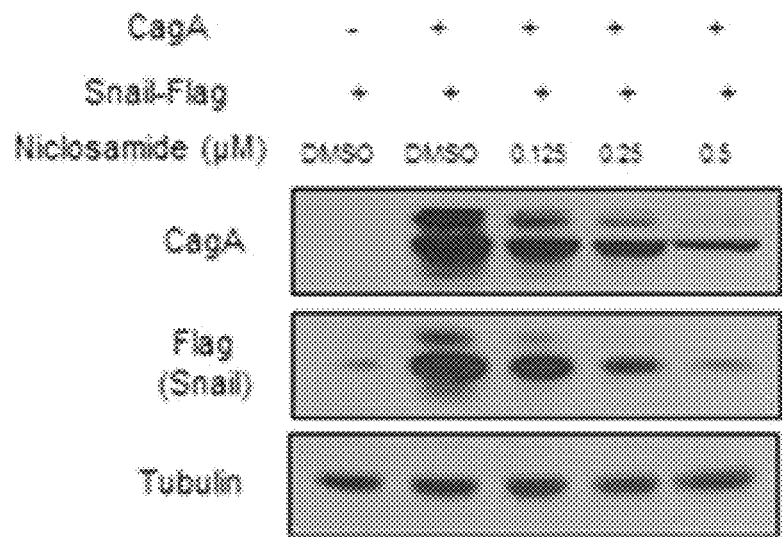

In view of the results of Examples 2~5 that niclosamide inhibited Wnt activity and EMT through Axin-GSK3 inhibition, and that CagA of *Helicobacter* (*Helicobacter pylori*) bound to GSK-3 similarly to Axin, the effect of GSK-3 binding and Snail induction by CagA of *Helicobacter pylori* by niclosamide was confirmed. It was confirmed that binding of CagA and GSK3 was inhibited by niclosamide similarly to Axin 2, when examining with immunoprecipitation after adding various amounts of niclosamide to this sample (FIG. 10A). In addition, it could be seen that Snail expression by CagA was inhibited when treating niclosamide after inducing CagA and Snail expression in the 293 cell (FIG. 10B). Through such a result, it could be seen that niclosamide inhibited the function of CagA performing function similar to Axin and thereby inhibited gastric cancer occurrence and inflammation by *Helicobacter*.

Through this result, it could be seen that niclosamide could be used as a new therapeutic agent for patients infected with *Helicobacter*.

INDUSTRIAL APPLICABILITY

According to the present invention, the familial adenomatosis polyposis (FAP) or multiple colonic polyps, *Helicobacter* inflammation, suffering from no treatment can be effectively treated by using niclosamide which is an FDA-approved safe drug.

Specific parts of the present invention have been described in detail so far, and therefore, to those skilled in the art, it will be clear that such a specific description is only a preferred embodiment and the scope of the present invention is not limited thereby. Accordingly, the substantive scope of the present invention is to be defined by the appended claims and their equivalents.

What is claimed is:

1. A method for treating an Axin-GSK3 interaction-related disease, comprising:
    administering to a subject in need thereof an effective amount of niclosamide or its pharmaceutically acceptable salt,
    wherein the Axin-GSK3 interaction-related disease is familial adenomatosis polyposis (FAP).

2. A method for treating an Axin-GSK3 interaction-related disease, comprising:
    administering to a subject in need thereof an effective amount of niclosamide or its pharmaceutically acceptable salt,
    wherein the Axin-GSK3 interaction-related disease is gastritis caused by *Helicobacter* infection.

* * * * *